(12) United States Patent
Lagaron Cabello et al.

(10) Patent No.: US 11,253,833 B2
(45) Date of Patent: Feb. 22, 2022

(54) SYSTEM AND METHOD FOR INDUSTRIAL ENCAPSULATION OF THERMOLABILE SUBSTANCES

(71) Applicants: BIOINICIA, S.L., Paterna (ES); CONSEJO SUPERIOR DE INVESTIGACIONES CIENTÍFICAS (CSIC), Madrid (ES)

(72) Inventors: José María Lagaron Cabello, Paterna (ES); Sergio Castro Reina, Paterna (ES); José Manuel Valle, Paterna (ES); David Galan Nevado, Paterna (ES)

(73) Assignees: BIOINICIA, S.L., Paterna (ES); CONSEJO SUPERIOR DE INVESTIGACIONES CIENTIFICAS (CSIC), Madrid (ES)

(*) Notice: Subject to any disclaimer, the term of this patent is extended or adjusted under 35 U.S.C. 154(b) by 314 days.

(21) Appl. No.: 16/475,214

(22) PCT Filed: Dec. 20, 2017

(86) PCT No.: PCT/ES2017/070833
§ 371 (c)(1),
(2) Date: Jul. 1, 2019

(87) PCT Pub. No.: WO2018/122427
PCT Pub. Date: Jul. 5, 2018

(65) Prior Publication Data
US 2019/0336931 A1    Nov. 7, 2019

(30) Foreign Application Priority Data
Dec. 30, 2016   (ES) .............................. ES201631725

(51) Int. Cl.
*B01J 13/04*      (2006.01)
*A61K 9/50*       (2006.01)
(Continued)

(52) U.S. Cl.
CPC ........... *B01J 13/043* (2013.01); *A61K 9/5042* (2013.01); *A61K 9/5063* (2013.01);
(Continued)

(58) Field of Classification Search
None
See application file for complete search history.

(56) References Cited

U.S. PATENT DOCUMENTS

2003/0230819 A1   12/2003   Park
2011/0171335 A1   7/2011    Bryner
(Continued)

FOREIGN PATENT DOCUMENTS

EP    2724775        4/2014
WO    WO200066256    11/2000
(Continued)

OTHER PUBLICATIONS

Jaworek et al, "Electrospraying Route to Nanotechnology: An Overview", Journal of Electrostatics, Elsevier Science Publishers V. Amsterdam, NL, vol. 66, No. 3-4, Jan. 28, 2008.
(Continued)

*Primary Examiner* — Jeffrey D Washville
(74) *Attorney, Agent, or Firm* — Hayes Soloway P.C.

(57) ABSTRACT

A facility for industrial drying and/or encapsulation of thermolabile substances comprising at least one injection unit (1) wherein the thermolabile substance is introduced, an encapsulating material when the facility is used to encapsulate, a solvent, additives and an injection gas flow for obtaining droplets from the thermolabile substance. It further comprises a drying unit (2) through which the droplets and a drying gas are introduced for evaporating the solvent and comprises a collection unit (3) configured to separate the microcapsules generated from the drying gas and which is selected from a cartridge filter collector, a cyclone collector
(Continued)

or a combination of the two. It also describes a method for the industrial encapsulation of thermolabile substances which is carried out at the proposed facility.

9 Claims, 12 Drawing Sheets

(51) Int. Cl.
    *B01J 2/02*     (2006.01)
    *F26B 3/08*     (2006.01)
    *F26B 3/12*     (2006.01)

(52) U.S. Cl.
    CPC ............... *A61K 9/5089* (2013.01); *B01J 2/02* (2013.01); *F26B 3/08* (2013.01); *F26B 3/12* (2013.01)

(56) References Cited

U.S. PATENT DOCUMENTS

| | | | |
|---|---|---|---|
| 2012/0263826 A1 | 10/2012 | Fang et al. | |
| 2012/0288533 A1* | 11/2012 | Livney | A23L 2/52 424/400 |
| 2013/0035279 A1* | 2/2013 | Venkataraman | A61K 8/11 514/1.1 |

FOREIGN PATENT DOCUMENTS

| | | |
|---|---|---|
| WO | WO2002060275 | 8/2002 |
| WO | WO2010039036 | 4/2010 |
| WO | WO2012058575 | 5/2012 |

OTHER PUBLICATIONS

Atmane Madene et al, "Flavour Encapsulation and Controlled Release—A Review", International Journal of Food Science and Technology, Blackwell Scientific Publications, Oxford, GB, vol. 41, Jan. 1, 2006.

Leja et al "Production of Dry Lactobacillus Rhamnosus GG Preparations by Spray Drying and Lyophilization in Aqueous Two-Phase Systems" Acta Scientiarum Polonorum, Technologia Alimentaria 8 4; 2009.

Jacobsen, "Food Enrichment with Omega 3 Fatty Acids" Woodhead Publishing Series in Food Science, Technology and Nutrition; 2013.

Ying, "Microencapsulated Lactobacillus Rhamnousus GG Powders: Relationship of Powder Physical Properties to Probiotic Survival during Storage" Journal of Food Science, 210 Nov.-Dec.; 75(9):E588-95.

* cited by examiner

FIG. 3

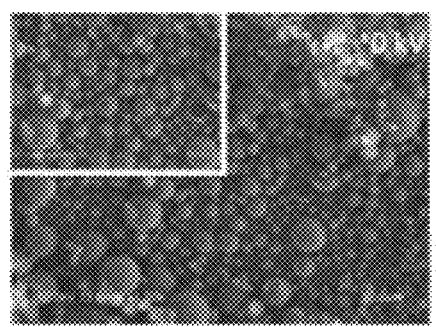 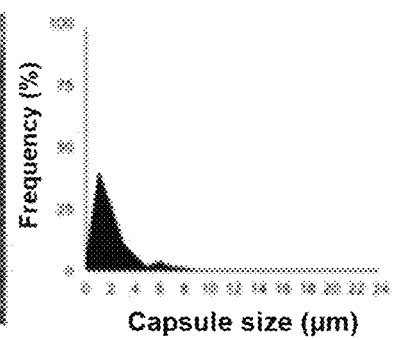
FIG. 7a  FIG. 7b
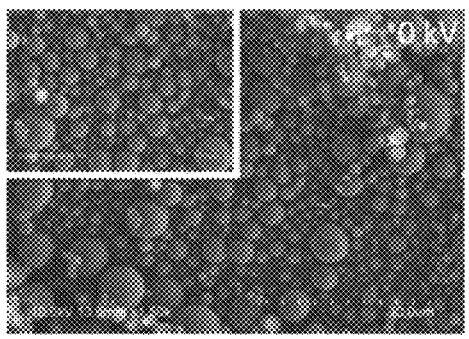 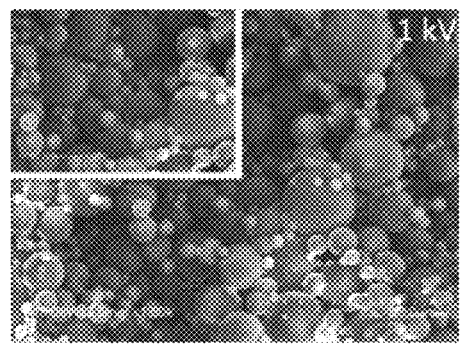
FIG. 8a  FIG. 8b

SYSTEM AND METHOD FOR INDUSTRIAL ENCAPSULATION OF THERMOLABILE SUBSTANCES

CROSS-REFERENCE TO RELATED APPLICATIONS AND PRIORITY

This patent application claims priority from PCT Application No. PCT/ES2017/070833 filed Dec. 20, 2017, which claims priority from Spanish Application No. P201631725 filed Dec. 30, 2016. Each of these patent applications are herein incorporated by reference in its/their entirety.

OBJECT OF THE INVENTION

The present invention falls within the pharmaceutical, biomedical, agricultural, cosmetics and food sectors. More specifically, it describes a facility and method for drying and/or encapsulation of thermolabile substances such as probiotic-type functional ingredients, polyunsaturated fatty acids, antioxidants, etc.

BACKGROUND OF THE INVENTION

The industrial techniques used for the microencapsulation or formation of microparticles of chemical products, in general, and food supplements, cosmetics and pharmaceuticals in particular, are spray drying and freeze-drying.

The spray drying technique consists of applying a counter-current of hot air to an aerosol generated by a sprayer containing the product to be mixed together with the encapsulant. In general, industrial units consist of a system for feeding the solution to be sprayed, a sprayer, a high-temperature drying chamber and a microparticle collector. In these cases the collector may be a cyclone collector, cartridge collector, etc. The technical problem of spray drying is that it is limited to working with stable products, since the high temperature used (generally higher than 100° C.) degrades the labile products.

Freeze-drying is a process that consists of freezing at low temperatures (−80° C.) followed by sublimation of the solvents by applying a vacuum. This technique makes it possible to work with labile products but requires the use of appropriate cryoprotective agents. Additionally, another technical problem associated with it is that it is very expensive to upscale due to its high electricity consumption and difficult insertion in a production chain, since it is executed in batch format.

Spray cooling techniques, which allow working with labile products, are also known in the state of the art. This technique uses low-melting-point vegetable oils (32-42° C.). The technique consists of heating the oil above its melting point and, after generating the aerosol, cooling it. The objective is to solidify the product into microcapsules. The low melting point of these materials reduces potential damage to thermolabile materials. The problem is that it is a reversible process and the product must be kept refrigerated. Additionally, this technique is limited by the type of encapsulating substance used, which must be low-melting-point oil. Additionally, it has other problems such as that it provides a lower barrier to oil-soluble molecules, which can produce unwanted off-flavours and odours. That is, oil-soluble molecules can penetrate the capsule (the capacity to maintain it encapsulated is limited). Therefore, its industrial use is currently limited.

So-called solution blowing uses a classic nebuliser, but applied to the manufacture of fibres from polymers. Inventions have also been described wherein this method is varied by also applying an electric field to obtain greater control of the diameter of the fibres generated. The difference in voltage is applied between different points that generate an electric field that interacts with the polymer to be nebulised.

Flow focusing is a similar technique wherein a fluid field instead of an electric field is used to obtain greater control over the jet generated and, therefore, over the size of the drops and microparticles. This enables greater control over the size of the microparticles than using conventional nebulisers. It consists of an injector, generally a tube, through which the working solution and a coaxial air flow that reduces the size of solution jet are injected, making it possible to control the size of the drop and, thus, of the microparticles generated. The small size of the drop generated by this technique facilitates drying at ambient temperature, maintaining the viability of labile products. However, the greatest technical problem associated with this technique, as with other, also experimental techniques (such as electrospraying), is that it is limited to low-production work due to the low performance of the injector.

Document US2011171335 and its patent family, for example, are known in the state of the art. It discloses an electrostretching system for manufacturing nanofibres consisting of a nebuliser with an electric field and a collector tray where the generated nanofibres are collected. With this system, nanofibres which are quick-drying due to their nano-size are generated and subsequently collected in a flat collector to which they are strongly adhered, which makes their industrialisation difficult.

Also known in the state of the art, for example, is the paper by K. Leja et. al, "*Production of dry Lactobacillus rhamnosus GG preparations by spray drying and lyophilization in aqueous two-phase systems*" in Acta Scientiarum Polonorum, Technologia Alimentaria 8 4 (2009), which describes an encapsulation method for encapsulating the probiotic bacteria *Lactobacillus rhamnosus* using the spray drying technique and the freeze-drying technique. This document is a scientific study that proves that capsule viability depends more on the polymer solution used than on the encapsulation method used. In the example, skimmed milk, PVP and a dextrin are used.

Also known is the paper by C. Jacobsen, "*Food Enrichment with Omega-3 Fatty Acids*" in Woodhead Publishing Series in Food Science, Technology and Nutrition (2013), which describes different techniques for microencapsulating omega-3 fatty acids with different encapsulating agents including, inter alia, the spray drying encapsulating technique. Likewise, the paper by D Y Ying, "*Microencapsulated Lactobacillus rhamnosus GG Powders: Relationship of Powder Physical Properties to Probiotic Survival during Storage*" in Journal of Food Science, 2010 November-December; 75 (9):E588-95 presents a study on the viability of *Lactobacillus rhamnosus* probiotic bacteria capsules with a Hylon VII starch. Said document describes, inter alia, an encapsulation method using the spray drying technique.

Patent document US20120263826A1 discloses a drinkable product comprising at least one aqueous liquid and capsules comprising entrapped probiotic bacteria including, inter alia, *Lactobacillus rhamnosus*. It also discloses some probiotic encapsulation techniques susceptible to being used and their drawbacks.

Document WO02060275 discloses a process for producing capsules or particles of micro and nanometric size using stable electrified coaxial jets of at least two immiscible liquids, for example, a first liquid that is surrounded by a second liquid, wherein the second liquid provides a barrier or protective coating. The method can be carried out in a dielectric atmosphere, preferably an atmosphere of inert gases or a vacuum.

DESCRIPTION OF THE INVENTION

The present invention proposes a facility for industrial drying and/or encapsulation of thermolabile substances. Moreover, it discloses a drying method with industrial encapsulation of thermolabile substances that makes it possible to overcome the described drawbacks of the solutions of the state of the art. This invention enables the generation of micro, submicro and nanoparticles in the case of their use for drying or of micro, submicro and nanocapsules in the case of their use for encapsulation. However, reference is made to microcapsules throughout the description and the preferred embodiment due to being the size obtained in the specific examples shown.

This invention enables the encapsulation of thermolabile substances, for example, to facilitate and homogenise the dosage of the product, to mask flavours, to protect the product inside the microcapsule, generally from humidity, light and ambient oxygen in order to achieve a controlled release of the active ingredient that remains inside the microcapsule or to increase its bioavailability.

"Thermolabile substance" is understood to be a substance that must be coated in order to maintain its stability. Examples of said substances in the present invention are microorganisms, enzymes, polyunsaturated fatty acids, antioxidants, vitamins, essential elements and any derived molecule or compound.

Examples of these means would be encapsulation of essential oils or enzymes in various matrices, including natural matrices such as zein, milk serum protein and pullulan, or synthetic matrices such as PEO (polyethylene oxide) or PVP (polyvinylpyrrolidone).

An object of the invention is the facility for industrial drying and/or encapsulation of thermolabile substances comprising:
- an injection unit, which is preferably a nebuliser or an electronebuliser,
- a drying unit, which is arranged after the injection unit, and
- a collection unit, arranged after the drying unit.

The facility enables industrial amounts of microcapsules of thermolabile material to be obtained at a controlled temperature, maintaining or increasing protection (protection of the thermolabile material content inside the microcapsule), provided by other low-production techniques, such as electrospraying and flow focusing.

The injection unit comprises an injector, at the inlet of which a solution comprising the thermolabile substance to be encapsulated, the encapsulating material, a solvent and necessary additives is introduced. Throughout the specification, when reference is made to the solution to be injected, reference is indistinctly made to a liquid (mixture of liquids or miscible liquid-solids), an emulsion (mixture of immiscible liquids) or a suspension (mixture of insoluble solids in a liquid).

The injection unit projects droplets whose size can be focused or controlled more efficiently through the application of an electric field at the injector outlet (in this exemplary embodiment, the injection unit can be an electronebuliser). To this end, in one exemplary embodiment, the injection unit comprises an electrode, typically circular, which is arranged at the injector outlet.

In the case in which the injection unit comprises an electric field at the injector outlet, the solution is electrically charged during spraying upon penetrating said electric field which is generated by applying high voltage, both in alternating current (AC) and direct current (DC). Adding the electric field enables better control over the size and monodispersity of the sizes of the droplets generated in the injector unit. Since thermolabile substances are going to be encapsulated and hot air is not going to be applied for drying, the droplets generated must be very small in order to reduce subsequent drying times.

As opposed to other solutions in the state of the art, in this facility hot air is not applied at the injector outlet of the injection unit. Therefore, better stability and protection results are achieved in terms of encapsulation of thermolabile compounds. This implies an improvement with respect to currently known solutions based on spray drying. It also has advantages over freeze-drying, since it is a continuous process that is executed in a single step under controlled, typically ambient temperature conditions.

The injection unit comprises a nebuliser-, sprayer- or aerosol-type injector, including pneumatic devices, piezoelectric devices, ultrasonic devices, vibratory devices, etc. In an embodiment of the present invention, the injection unit comprises a pneumatic nebuliser of the type comprising an inlet for a liquid solution and two inlets for injection gas. In this exemplary embodiment, the injection unit comprises two inlets for injection gas, of which one inlet for injection gas is arranged coaxially to the solution inlet and an additional inlet for injection gas is arranged with a certain degree of inclination to the solution inlet.

That is, one of the inlets for injection gas is arranged such that the injection gas flow is projected in a coaxial direction to the solution flow, as in any nebuliser, and the other inlet is arranged such that the injection gas flow is projected at a certain angle with respect to the solution flow, impacting against the liquid jet flow. This enables greater reduction in drop size. In this case, the facility may be used with a gas flow that can be air, nitrogen or other gas and mixtures thereof. For example, an inert gas would be used to work in a protective atmosphere or when using a flammable solvent.

As described, the injection unit projects droplets whose size depends on the type of injector, specifically in the preferred case in which the injection unit comprises a nebuliser such as that described, the size depends on the flow rate of a solution current, on the flow rate of an injection gas current and on the properties of the solution, mainly surface tension, conductivity and viscosity.

Additionally, the present invention proposes the use of an external electric field for greater control of the size of the droplets and their monodispersity. To this end, in one exemplary embodiment, the injection unit comprises an electrode, typically circular, arranged right at the injector outlet. The liquid, during spraying, is electrically charged upon penetrating said electrode, which is working at high voltage, both in direct and alternating current.

In the drying unit, the droplets formed in the injection unit are dried at a controlled temperature. During the movement of the droplets through the drying unit, the solvent of the solution with which the microcapsules have been formed evaporates. After circulating completely through the drying unit, the solvent evaporates completely, giving rise to the desired microcapsules which are subsequently collected by the collection unit. It should be noted that the unit can dry and encapsulate at a controlled temperature, typically at ambient or sub-ambient temperature, without the need to apply heat at a high temperature to vaporise the solvent. In the case in which thermolabile substances at ambient temperature are used, the facility and method make it possible to work at sub-ambient temperature, such as for example 5° C.

The drying unit comprises a receptacle. The injection unit and a drying gas inlet are at one end of said receptacle. The collection unit is at the opposite end. The drying gas is introduced in the drying unit at a controlled temperature. The drying gas may be air, nitrogen or other gas and mixtures thereof.

The arrangement of the drying unit with respect to the injection unit may be both coaxial thereto and at any angle of inclination therebetween. The present invention preferably proposes a coaxial arrangement. The drying gas is introduced in the drying unit at a controlled temperature, typically at ambient temperature. Since the drying gas is introduced in the drying unit in a certain direction, it drags the droplets generated in the injection unit with it. As it circulates through the drying unit, the solvent in the droplets evaporates, thereby giving rise to the desired microcapsules.

The geometry of the drying device a priori may be any which allows an adequate residence time for drying the drops. An optimum geometry would be a cylinder with a variable circular cross-section, with an increasing cross-section from the inlet to the outlet. This enables greater dragging in the area in which the drops are largest and this allows longer residence time for a certain length.

In another exemplary embodiment, the facility comprises a drying unit comprising a secondary inlet, arranged perpendicularly to its longitudinal axis. These drying units comprise a sleeve and a secondary gas flow. This secondary gas flow is injected in a direction perpendicular to the surface of the drying unit through holes or pores arranged on the surface of the drying unit. This makes it possible to reduce loss of material from adhesion to the walls of the drying unit. The secondary gas may be air, nitrogen or other gas and mixtures thereof.

The drying gas flow must be sufficient to absorb all the solvent injected from the injection unit. When aqueous solutions are used, the maximum amount of water that the drying gas can absorb is smaller the greater the relative humidity of the drying gas used.

That is, if, for example, air from outside the facility is used as the drying gas and the method is being carried out on a rainy day, with a high degree of humidity, the amount of drying gas required to evaporate a fixed solvent volume will be greater than if the method is carried out on a dry day (since the outside air will have a lower relative humidity).

Likewise, a smaller drying unit cross-section size is selected, which generally has a cylindrical configuration, when wanting to achieve greater dragging and collection of microcapsules. This is because if the drying gas flow rate is maintained and the drying unit cross-section is decreased, the dragging speed through the inside of said drying unit increases.

Furthermore, it should be noted that higher gas speeds (obtained, for example, by decreasing the size of the cross-section of the drying unit as explained previously) give rise to shorter residence times and, therefore, shorter drying times. This could make it difficult to dry larger microcapsules. Therefore, the facility is designed so as to have a specific compromise solution in which dragging speed and residence time for each solution are optimised. The facility will be designed maintaining compromise dimensions to optimise dragging speed and drying time in accordance with the solution used for encapsulation. Drying time is also called residence time, since it relates to the time during which the droplets remain in the drying unit.

The design of the drying unit depends on the solvent used and on the thermolabile substance to be encapsulated, since both factors strongly influence the size of the drop generated by the injection unit and the evaporation kinetics thereof. The optimum drying unit diameters and lengths that enable optimum speeds and residence times for, for example, a facility with a manufacturing yield of approximately 1 kg/h of dry or encapsulated product typically range, but are not limited to, between 2 and 200 cm in diameter and between 20 cm and 20 m in length, respectively. Larger industrial facilities may use foreseeably greater diameters and lengths.

The proposed facility is therefore optimal for industrial use due to its high yield and makes it possible to carry out the method for obtaining microcapsules of thermolabile substances continuously and in a single step.

With the aim of controlling the evaporation of the solvent more efficiently, the facility, more specifically the drying unit, may operate at different pressures, even in a vacuum.

The collection unit enables the efficient separation of the microcapsules generated from the drying gas. The collection unit may comprise at least one cyclonic separation, centrifugal separation or filtration device, with or without electrostatic charge. The collection unit is preferably a cartridge filter collector or a cyclonic collector. In one exemplary embodiment, the collection unit comprises a cyclone collector and a cartridge filter arranged in series. This makes it possible to collect large microcapsules in the cyclone collector and smaller microcapsules in the cartridge filter collector.

In the case of using a flammable solvent, inert gases, typically nitrogen, will preferably be used, and the facility in which the method is carried out must be manufactured from ATEX-classified materials and units, comprising venting and suppression devices.

In the case that the device is used to obtain a dry product or aseptic encapsulation, the injection gas and drying gas must be filtered, typically making them pass through a HEPA H14 filter or similar, or sterilised, typically by means of exposure to ultraviolet light, ethylene oxide, radiation, etc., or a combination thereof. In this case, both the preparation of the solution and handling of the collected product are carried out in a clean room sterile facility or similar.

Likewise, in a preferred embodiment, the collection unit comprises a solvent condensing device, arranged at the drying gas outlet, downstream from the collection unit. In another exemplary embodiment, the drying gas collected at said drying gas outlet is recirculated to resupply the injection unit and/or drying unit. Typically, the recovery of the solvent or the closed-loop resupply thereof is of special interest when the solvent or drying gas used is expensive or for security or sterility reasons. The facility may also include a device for pre-drying the incoming gas to facilitate drying of the droplets or the closed-loop recirculation thereof. This case is a preferred embodiment when the drying gas is ambient air.

As described above, another object of the invention is a method for the industrial encapsulation of thermolabile substances carried out in a facility such as that described above. Said method comprises at least one stage of preparation of a polymer solution comprising a thermolabile structure to be encapsulated, an encapsulating precursor and an organic or aqueous solvent preferably selected from ethanol, isopropanol, water and a combination thereof.

The method further comprises a stage of forming droplets from the previously obtained polymer solution in the presence of an injection gas flow. Subsequently, the method comprises a stage of drying the droplets obtained in the drying unit at a controlled temperature and a stage of collecting the corresponding microcapsules obtained after drying by means of the collection unit.

DESCRIPTION OF THE FIGURES

As a complement to the description being made, and for the purpose of helping to make the characteristics of the invention more readily understandable, in accordance with a preferred example of a practical embodiment thereof, said description is accompanied by a set of drawings constituting an integral part thereof which, by way of illustration and not limitation, represent the following.

Figure 3:
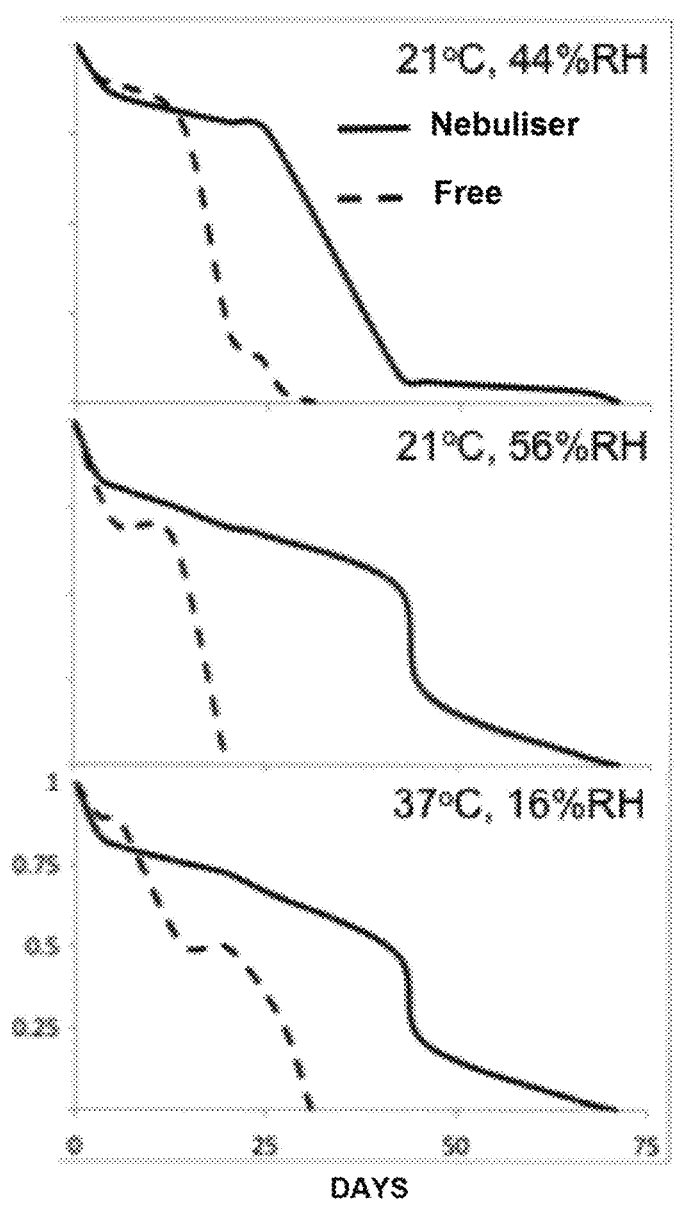

FIG. 3. Shows a comparative viability study normalised at 1 obtained by infrared transmittance spectroscopy on KBr pellets of the microcapsules and of the non-encapsulated omega-3 obtained in accordance with the examples represented in FIGS. 2a-2d;

FIGS. 7a-7b. Show a SEM micrograph and a particle size graph obtained for encapsulating *Lactobacillus rhamnosus* in a facility whose injection unit is a nebuliser;

FIGS. 8a-8h. Show SEM micrograph and particle size graphs obtained for one exemplary embodiment wherein *Lactobacillus rhamnosus* is encapsulated in a facility whose injection unit is an electronebuliser and wherein milk serum protein has been used as an encapsulating precursor, Tego® as a surfactant and whole milk as a liquid matrix.

PREFERRED EMBODIMENT OF THE INVENTION

What follows is a description of exemplary embodiments of the facility for industrial drying and/or encapsulation of thermolabile substances that refer to a manufacturing scale of 1 kg/h of dry or encapsulated product. It is expected that facilities that generate a higher production volume may require greater, scalable facility and processing parameters to those described and therefore the proposed parameters must not be considered limiting in nature. Likewise, exemplary embodiments of methods for the industrial encapsulation of thermolabile substances in the proposed facility are also described.

Figure 1A:
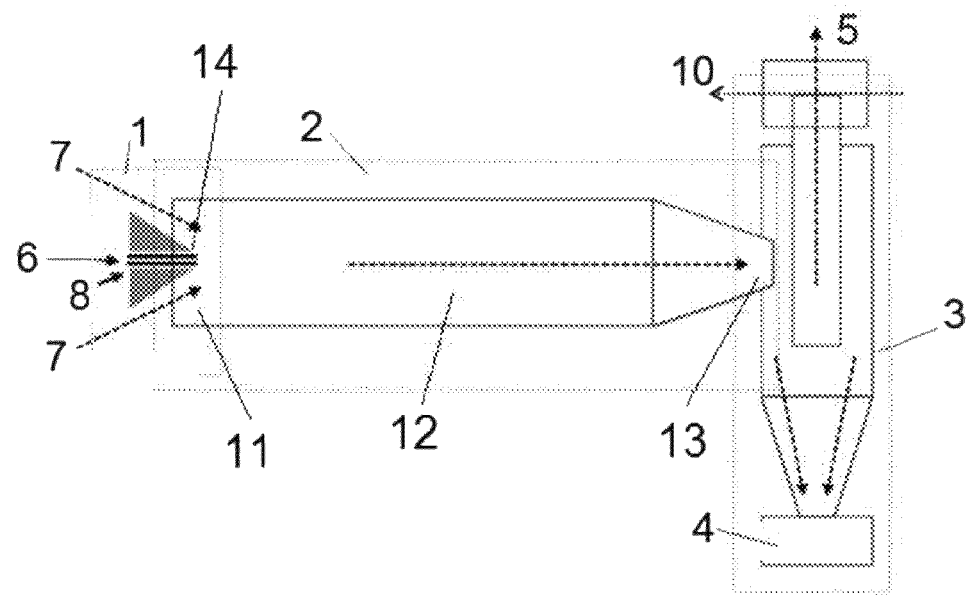
FIG. 1a. Shows an exemplary embodiment of the facility for industrial drying and/or encapsulation of thermolabile substances wherein the injection unit (1), drying unit (2) and collection unit (3) can be seen.
Figure 1B:
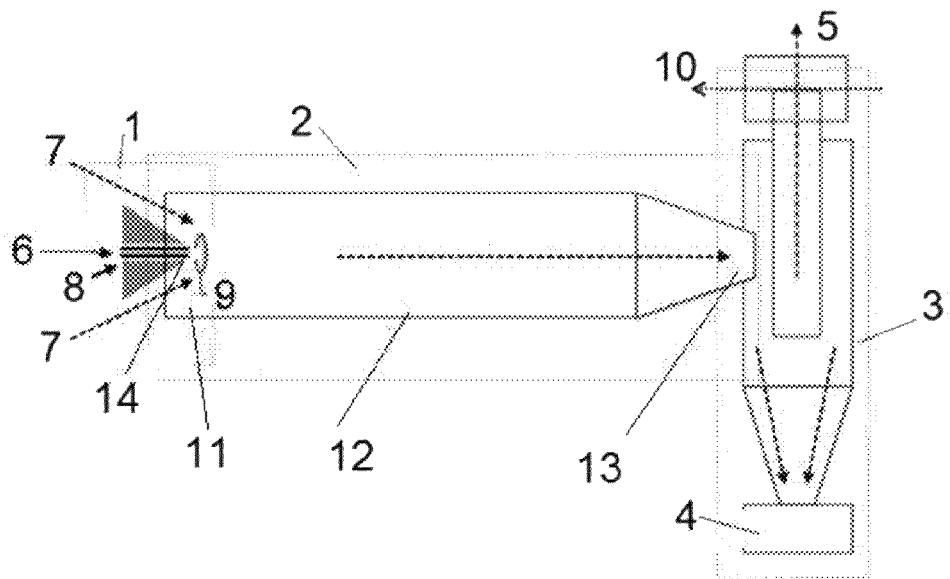
FIG. 1b. Shows another exemplary embodiment of the facility for industrial drying and/or encapsulation of thermolabile substances comprising an electric circuit (9) arranged at the droplet outlet (14) of the injection unit (1)
Figure 2A:
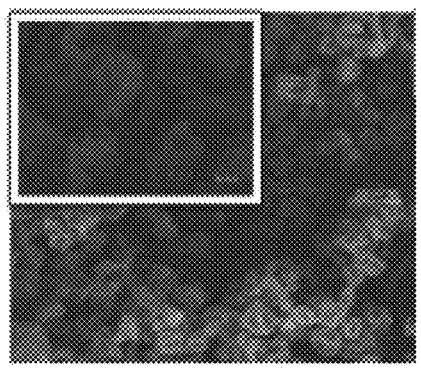
FIGS. 2a-2d. Show SEM micrographs and particle size graphs obtained for an exemplary embodiment wherein Omega-3 is encapsulated in a facility whose injection unit is a nebuliser and wherein zein and pullulan have been used as an encapsulating precursor.
Figure 2B:
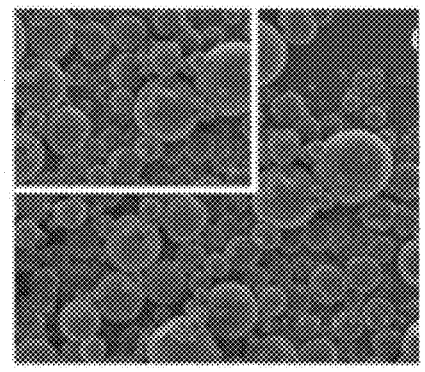
Figure 2C:
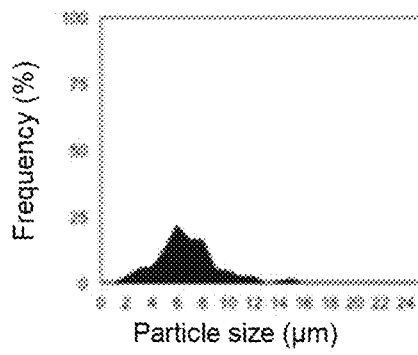
Figure 2D:
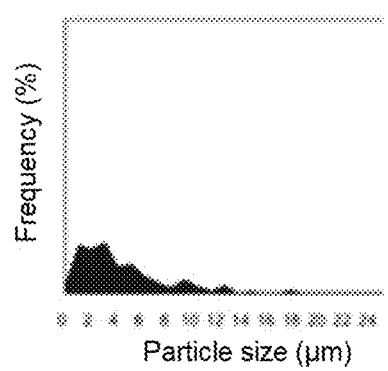
Figure 4A:
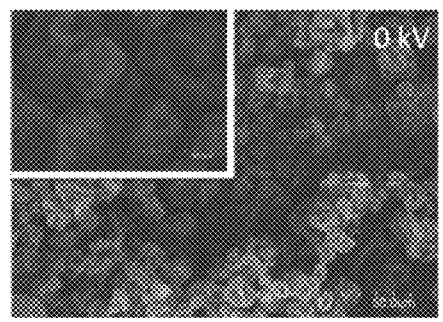
FIGS. 4a-4h. Show SEM micrographs and particle size graphs obtained for one exemplary embodiment wherein omega-3 is encapsulated in a facility whose injection unit is an electronebuliser and wherein ethanol 70% has been used as a solvent and zein as an encapsulating precursor.
Figure 4B:
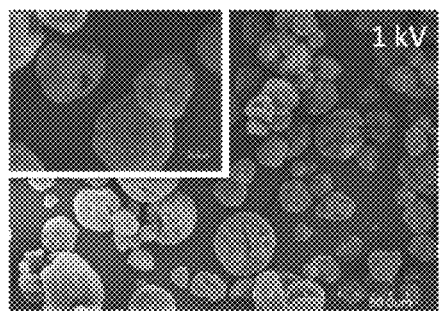
Figure 4C:
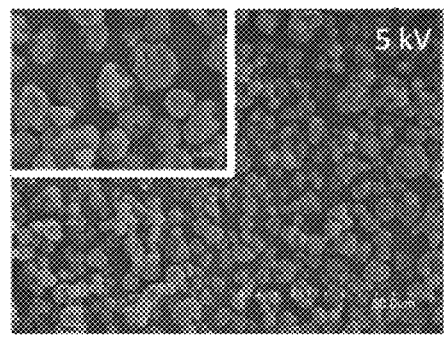
Figure 4D:
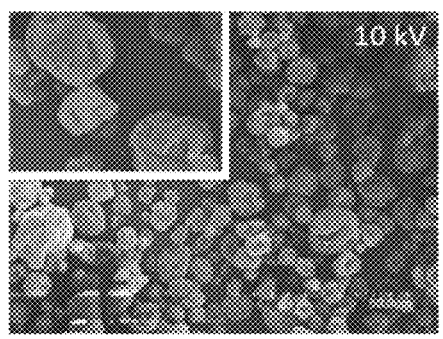
Figure 4E:
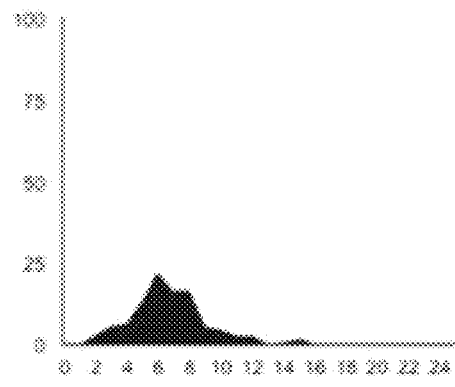
Figure 4F:
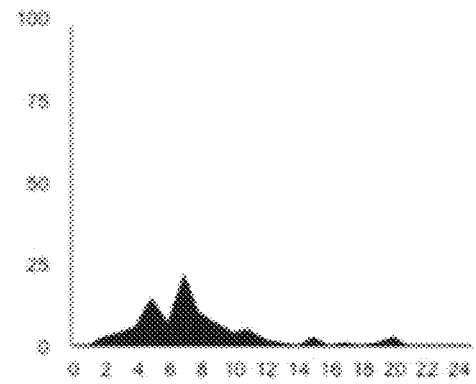
Figure 4G:
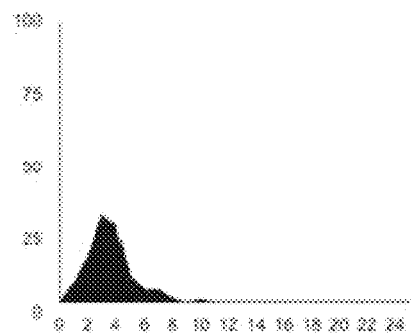
Figure 4H:
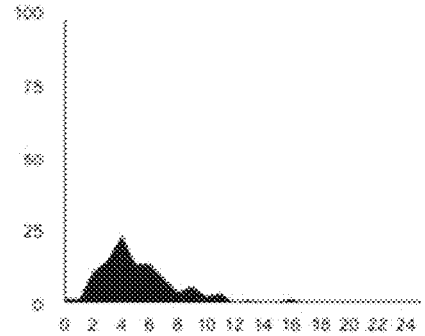
Figure 5A:
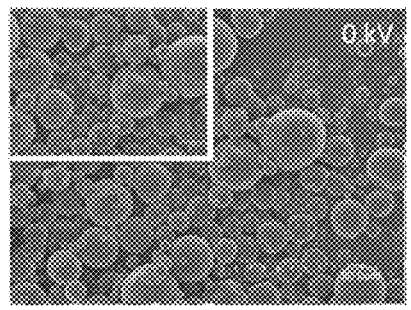
FIGS. 5a-5h. Show SEM micrographs and particle size graphs obtained for one exemplary embodiment wherein omega-3 is encapsulated in a facility whose injection unit is an electronebuliser and wherein water has been used as a solvent and pullulan as an encapsulating material and Tego® as a surfactant.
Figure 5B:
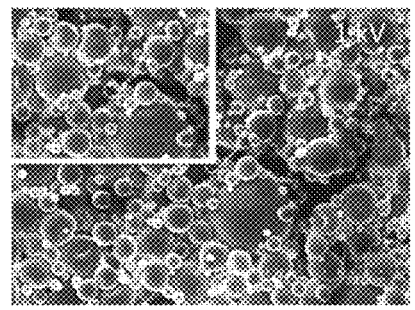
Figure 5C:
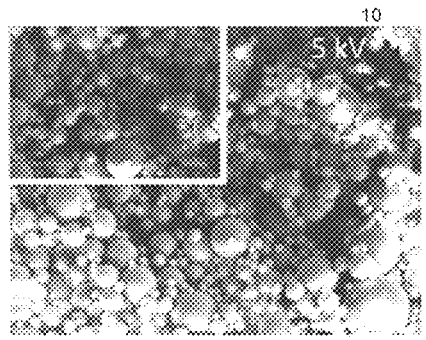
Figure 5D:
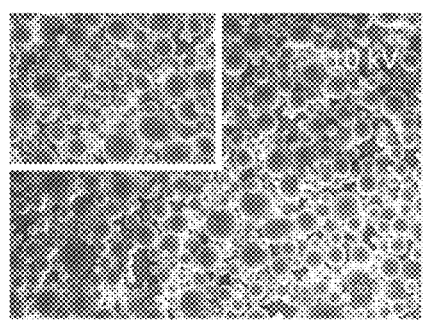
Figure 5E:
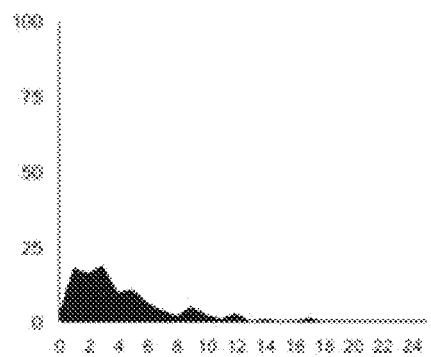
Figure 5F:
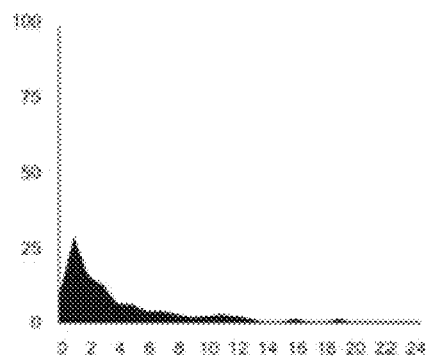
Figure 5G:
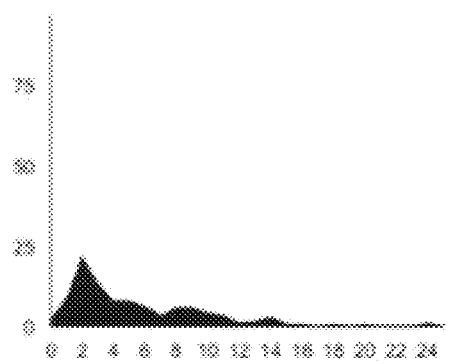
Figure 5H:
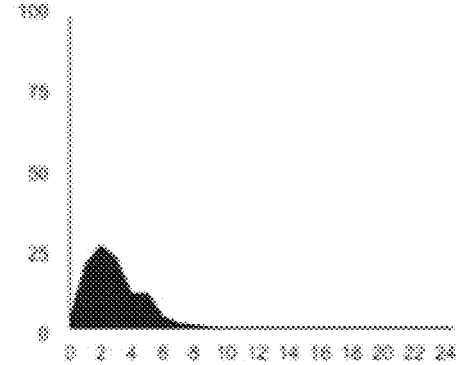

As shown in FIG. 1, the facility comprises at least:
one injection unit (1) comprising at least one injector with at least one inlet for a solution (6) (which already includes the thermolabile substance to be encapsulated, the encapsulating material in the case that it is used for an encapsulation process, a solvent and necessary additives), an inlet for the injection gas (8) and an outlet for droplets (14) for the solution that exits sprayed in droplets;

one drying unit (2) arranged after the injection unit (1) and comprising at least one drying gas inlet (7) and an inlet for the droplets (11) that exit the injection unit (1); and comprising a longitudinal receptacle (12) which preferably has a cylindrical configuration, and which is arranged with its longitudinal direction horizontal and which has sufficient length to allow the evaporation of all the solvent of the droplets; and has a microcapsule and drying gas outlet (13) through which microcapsules pass (which are the droplets without the solvent, which has evaporated during its circulation through the drying unit);

one collection unit (3) arranged after the drying unit, which is configured to separate the microcapsules generated from the drying gas (it drags the solvent which has evaporated in the drying unit) and comprises an outlet for said generated microcapsules (4) and an outlet for the drying gas (5).

In one exemplary embodiment of the invention, the collection unit further comprises a solvent condensing device (10), arranged at the drying gas outlet (5), downstream from the collection unit (3). In another exemplary embodiment, the facility may comprise a drying gas recirculation device that makes it possible to redirect the drying gas towards the injection unit (1) and/or the drying unit (2).

In one exemplary embodiment, the injector of the injection unit is a nebuliser consisting of a sprayer such as that described above. The injection gas flow rate, in one exemplary embodiment, is between 1 and 500 LPM. The flow rate of the injected liquid, which can be found in the form of solution, emulsion or suspension, ranges preferably between 1 ml/h and 50 L/h.

In one exemplary embodiment, the facility additionally comprises a high-voltage electric circuit (9) at the outlet of the injection unit (1). The voltage used in the circuit depends on the flow rate of the injected solution and ranges between 100 kV and 500 kV. The effect achieved is that of charging the solution, focusing the droplet beam and collaborating in the formation of the droplets, improving control over the size thereof. It also influences the monodispersity of the droplets, since it generates a more homogeneous size distribution. A high monodispersity may be essential to the final product, since it enables greater homogeneity in the protection or release of the thermolabile material that has been encapsulated and, therefore, greater control over the encapsulation process.

In one exemplary embodiment, the drying gas flow rate ranges between 10 and 100,000 m$^3$/h. In the case of working with aqueous solutions, the drying is more complex because the drying gas is humidified and, therefore, it takes longer to remove the water from the solution in the drying unit.

To this end, in these cases the facility may additionally comprise a device for pre-drying the drying gas in order for said drying gas introduced in said unit to be drier, thereby increasing the yield of the facility. In those cases where ethanol, isopropanol and other non-aqueous solutions are used drying is easier because the drying gas, typically air, does not include a solvent. Therefore, the drying gas is free from ethanol and, therefore, does not affect the speed of evaporation of the ethanol in the drying unit.

In order to control the evaporation of the solvent in the facility more efficiently, the drying unit further comprises, in one exemplary embodiment, a pressure control device that makes it possible to work at different pressures, even in a vacuum.

Preferably, the facility is designed to obtain a microcapsule size ranging between 1 and 50 micrometres in diameter. For typical drying flow rates between 10 and 100,000 m$^3$/h, the optimum diameters and lengths of the drying unit range between 20 and 200 cm in diameter and between 20 cm and 20 metres in length. In an exemplary embodiment detailed below, the drying unit comprises a cylindrical receptacle 60 centimetres in diameter and 2 metres in length with cone-shaped inlets and outlets.

Another object of the present invention is a method for the industrial encapsulation of thermolabile substances carried out in the previously described facility. This method comprises the following stages:

a) preparing a polymer solution comprising:
  a thermolabile substance to be encapsulated,
  an encapsulating precursor,
  an aqueous or organic solvent and that will preferably be selected from ethanol, isopropanol, water and a combination thereof, and
b) forming droplets from the polymer solution obtained in stage (a) in the presence of an injection gas flow;
c) drying the droplets obtained in stage (b) in the drying unit at ambient temperature and using an air flow rate ranging between 10 m$^3$/h and 100,000 m$^3$/h to obtain microcapsules; and
d) collecting the microcapsules obtained in stage (c) by means of the collection unit.

Throughout the specification, it is understood that the polymer solution of stage (a) may be a solution as such, i.e. a mixture of liquids or a mixture of miscible liquid-solid solids; an emulsion, i.e. a mixture of immiscible liquids; or a suspension, i.e. a mixture of insoluble solids in a liquid.

Preferably, the encapsulating precursor of stage (a) is selected from animal, vegetable and microbial proteins. More preferably, the encapsulating precursor of stage (a) is selected form milk serum, caseins, natural polypeptides or obtained from the genetic modification of microorganisms, collagen, soy protein and zein. Even more preferably, the encapsulating precursor of stage (a) is selected between zein and milk serum protein.

In another exemplary embodiment, the encapsulating precursor of stage (a) are oligosaccharides selected from lactose, sucrose, maltose and fructo-oligosaccharides. More preferably, the encapsulating precursor of stage (a) is a fructo-oligosaccharide.

In another exemplary embodiment, the encapsulating precursor of stage (a) are polysaccharides selected from alginate, galactomanan, pectins, chitosan, rubbers, carragenates, pullulan, FucoPol, starch, dextran, maltodextrin, cellulose, glycogen and chitin. More preferably, the encapsulating precursor of stage (a) is selected from pullulan, dextran, maltodextrin, starch and any combination thereof.

Optionally, in stage (a) additives are used to optimise the properties of the solution. In the present invention, additive is understood to be a substance selected from a plasticiser, tensioactive agent, emulsifier, surfactant, antioxidants or any combination thereof. Examples of additives in the present invention would be the surfactants commercially named Tween®, Span® and Tego®, more preferably Tego®, since their use in food is allowed.

Preferably, stage b) of forming droplets is carried out by applying a voltage between 0.1 kV and 500 kV to the solution and drying gas flow at the outlet of the injection unit. More preferably, stage b) of forming droplets is carried out by applying a voltage between 5 kV and 60 kV to the solution and drying gas flow at the outlet of the injection unit. Preferably, the voltage applied ranges between 5 kV and 15 kV.

In another exemplary embodiment, stage b) of forming droplets is carried out applying a voltage in alternating current.

In one exemplary embodiment, the injection gas flow rate of stage (b) ranges between 1 and 500 LPM.

Preferably, in stage (c) drying gas flow rates ranging between 10 m$^3$/h and 100,000 m$^3$/h are used to obtain microcapsules between 1 and 20 micrometres in diameter.

The thermolabile compounds to be protected are preferably microorganisms, antioxidants, viruses, enzymes, polyunsaturated fatty acids, essential elements or any derived molecule or compound derived.

According to another preferred embodiment, the thermolabile compounds are selected from the group formed by antioxidants (vitamin C, vitamin E, carotenoids, phenolic compounds such as flavonoids and resveratrol) and natural or synthetic antioxidant concentrates or isolates, biological organisms such as cells of value to biomedicine and probiotics (such as *Lactobacillus* and *Bifidobacterium*), other microorganisms such as *Cyanobacterium, Rhodobacterals* and *Saccharomyces*, prebiotics (lactulose, galacto-oligosaccharides, fructo-oligosaccharides, malto-oligosaccharides, xylo-oligosaccharides and soy oligosaccharides), symbiotics, functional fibres, oleic acid, polyunsaturated fatty acids (omega-3 and omega-6) and other marine oils, phytosterols, phytoestrogens, protein ingredients (AON and its derivatives, lactoferrin, ovotransferrin, lactoperoxidase, lysozyme, soy protein, immunoglobulins, bioactive peptides) and pharmaceutical products such as nutraceutics and other value-added preparations and substances for the pharmaceutical, biomedical, cosmetics, food and chemical industries which may be destabilised by ambient, processing or storage conditions in its commercial presentation or any combination thereof.

More preferably, the thermolabile compounds are selected from the group formed by:
  carotenoids and polyphenols
  probiotics (*Lactobacillus* and *Bifidobacterium*)
  cells of biomedical interest for bone and tissue regeneration
  polyunsaturated fatty acids (omega-3 and omega-6)
  enzymes and other proteins of technological value selected from lactoferrin, ovotransferrin, lactoperoxidase, lysozyme, soy protein and immunoglobulins
  bioactive peptides selected from antihypertensive and antimicrobial peptides.

Below, various exemplary methods are shown wherein the thermolabile substances to be encapsulated are omega-3 and probiotics. In a specific exemplary embodiment, the selected probiotic was *Lactobacillus rhamnosus*.

In examples 1.1 and 1.2, non-limiting methods for encapsulating omega-3 fatty acid are described and corresponding viability studies are described.

Example 1.1 Encapsulation of Omega-3 Using a Nebuliser as an Injector

Figure 6A:
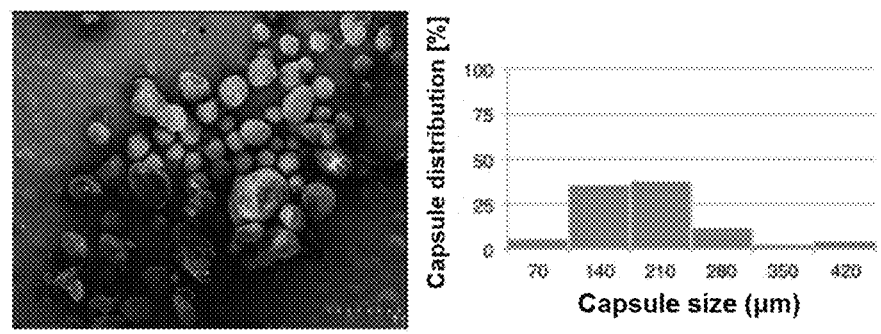
FIGS. 6a-6f. Show SEM micrographs and particle size graphs obtained by means of different existing commercial omega-3 encapsulation methods.
Figure 6B:
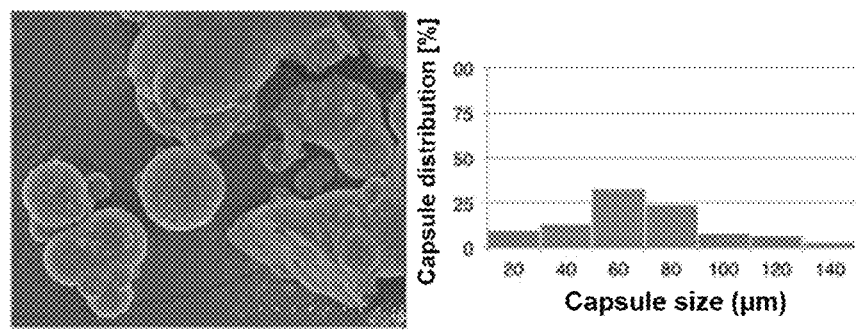
Figure 6C:
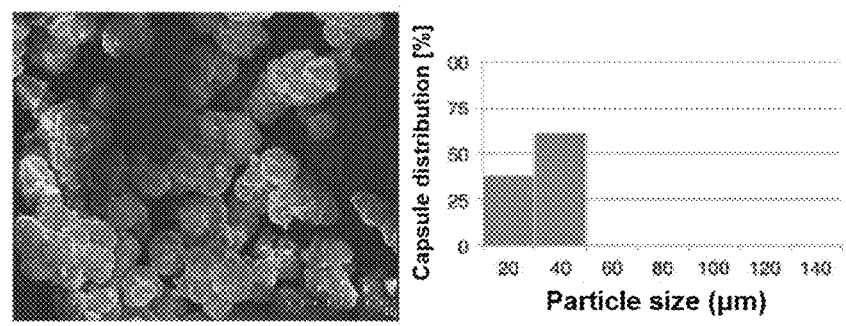
Figure 6D:
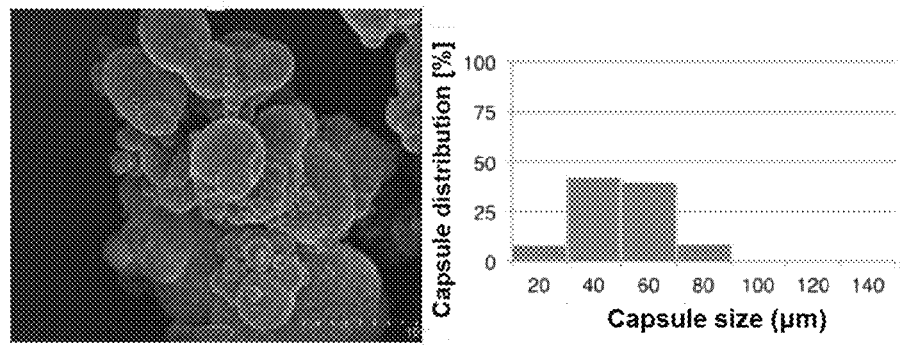

In this example, a conventional nebuliser was used as an injection unit. Additionally, different natural polymer candidates are used to encapsulate omega-3 fatty acid and thus prevent its oxidation and the transmission of odours and flavours to food in direct contact, such as for example zein, pullulan, milk serum protein and modified maltodextrins (Pineflow® and Nutriose®). The capsules generated using the materials with the greatest potential, zein and pullulan, can be seen in the SEM micrographs of FIGS. 2*a* and 2*b*, respectively. The optimum sizes can be observed in FIGS. 2*c* and 2*d*, within the range of 2-10 microns, in size distribution graphs, corresponding respectively to the micrographs of FIGS. 2*a* and 2*b*. The experimental parameters and ranges of use are shown in tables 1 and 2, respectively.

TABLE 1

Experimental parameters and operating ranges of the method of example 1.1 using zein.

| | Minimum value | Maximum value |
|---|---|---|
| Parameters | | |
| Solution flow rate | 1 mL/h | 50 L/h |
| Injection gas flow rate | 1 LPM | 500 LPM |
| Solution | | |
| Omega-3 fatty acid | 0.05% w/w | 50% w/w |
| Ethanol 70% | solvent | solvent |
| Zein | 0.05% w/w | 50% w/w |

TABLE 2

Experimental parameters and operating ranges of the processing of example 1.1 using pullulan.

| | Minimum value | Maximum value |
|---|---|---|
| Parameters | | |
| Solution flow rate | 1 mL/h | 50 L/h |
| Air flow rate | 1 LPM | 500 LPM |
| Solution | | |
| Omega-3 | 0.05% w/w | 50% w/w |
| Water | solvent | solvent |
| Pullulan | 0.05% w/w | 50% w/w |
| Tego | 0.01% w/w | 10% w/w |

FIG. 3 shows a viability study where it can be observed how encapsulation by means of the facility of the invention visibly improves the viability of the product (Omega-3) under all the temperature and relative humidity conditions studied. The viability curves indicate that the described facility and method enable microcapsules with viabilities substantially higher than those of the free product to be obtained.

Example 1.2 Encapsulation of Omega-3 Using an Electronebuliser as an Injector In this exemplary embodiment, an electronebuliser was used as an injection unit and the same natural polymers of example 1.2 were used. In FIGS. 4*a*-4*d* the effect of the technical field on microcapsule geometry can be observed. More specifically, said figures show the microcapsules when an electric field is not applied (FIG. 4*a*), when the electric field is 1 kV (FIG. 4*b*), when the electric field is 5 kV (FIG. 4*c*) and when the electric field is 10 kV (FIG. 4*d*). Therefore, it can be observed how an optimised electric field enables greater control over microcapsule geometry, allowing highly spherical geometries, high monodispersity and size control. In the case of zein, wherein in example 1.1 it can be observed that the capsules collapse, it can now be observed how they maintain their spherical structure due to the charge provided by the electric field, which prevents the droplets from collapsing during the evaporation of the solvent. FIGS. 4*e*-4*h* show the distribution of particle size for each of the micrographs of FIGS. 4*a*-4*d*, respectively. The experimental parameters and ranges of use are shown in table 3.

TABLE 3

Experimental parameters and operating ranges of the method of example 1.2 using a solution comprising ethanol 70% and zein.

| | Minimum value | Maximum value |
|---|---|---|
| Parameters | | |
| Solution flow rate | 1 mL/h | 50 L/h |
| Injection gas flow rate | 1 LPM | 500 LPM |
| Drying gas flow rate | 10 $m^3/h$ | 100,000 $m^3/h$ |
| Voltage | 0 | 500 kV |
| Solution | | |
| Omega-3 fatty acid | 0.05% w/w | 50% w/w |
| Ethanol 70% | solvent | solvent |
| Zein | 0.05% w/w | 50% w/w |

In the event of using a solution which, in addition to the thermolabile substance omega-3, comprises water, pullulan and Tego®, results are obtained such as those shown in FIGS. 5*a*-5*d*, where the results have been represented in accordance with the electric field (the values of said electric field have been made to vary as described earlier: without electric field, with a 1 kV electric field, with a 5 kV electric field and with a 10 kV electric field). FIGS. 5*e*-5*h* show particle size distribution for each of the micrographs of FIGS. 5*a*-5*d*, respectively. The experimental parameters and ranges of use for obtaining the described results are shown in table 4.

TABLE 4

Experimental parameters and operating ranges of the processing of example 1.2 using a solution comprising water, pullulan and Tego ®.

| | Minimum value | Maximum value |
|---|---|---|
| Parameters | | |
| Solution flow rate | 1 mL/h | 50 L/h |
| Injection gas flow | 1 LPM | 500 LPM |
| Drying gas flow rate | 10 $m^3/h$ | 100,000 $m^3/h$ |
| Voltage | 0 kV | 500 kV |
| Solution | | |
| Omega-3 fatty acid | 0.05% w/w | 50% w/w |
| Water | solvent | solvent |
| Pullulan | 0.05% w/w | 50% w/w |
| Tego | 0.01% w/w | 10% w/w |

FIGS. 6a-6f show SEM micrographs and particle size distribution corresponding to different methods for obtaining existing commercial microcapsules. FIGS. 6a-6d show results obtained using methods known in the state of the art. More specifically, FIG. 6a shows the results obtained using BASF (spray-drying in a nitrogen atmosphere), FIG. 6b shows the results obtained using LIFE (spray-drying in air), FIG. 6c shows the results obtained using MEG (spray-drying in air) and FIG. 6d shows the results obtained using STEPAN (spray-drying in a nitrogen atmosphere).

Figure 6E:
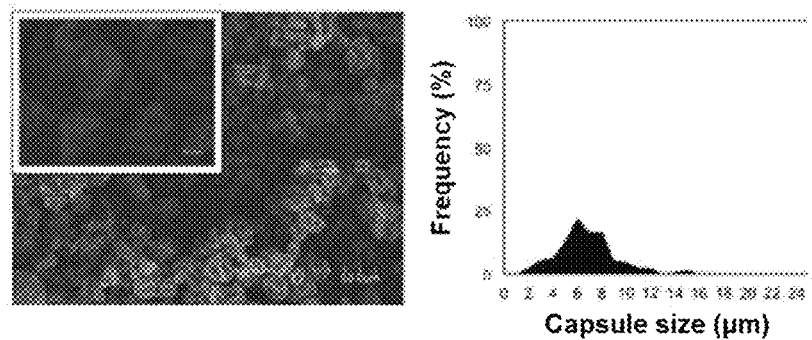
Figure 6F:
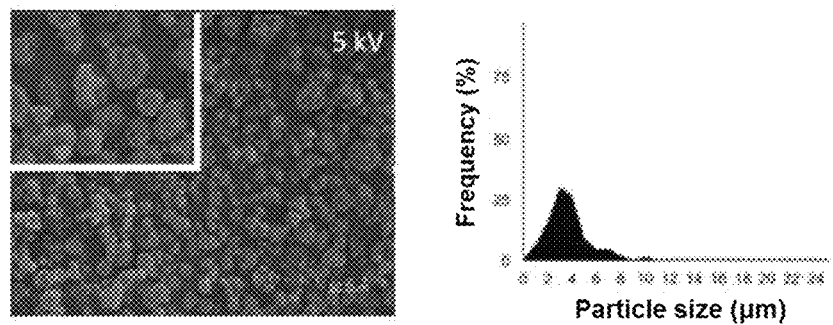
Figure 8C:
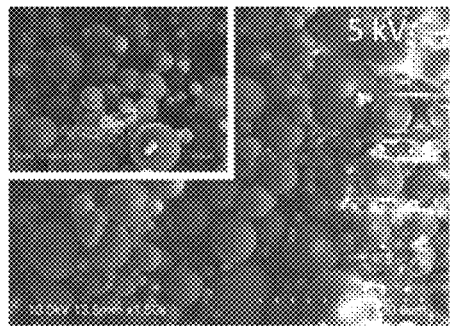
Figure 8D:
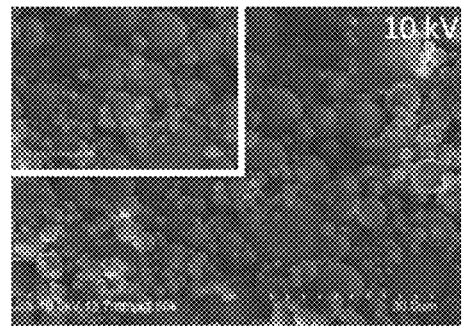
Figure 8E:
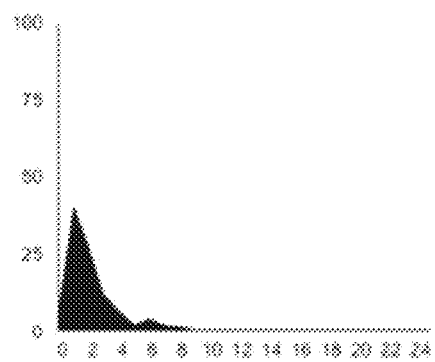
Figure 8F:
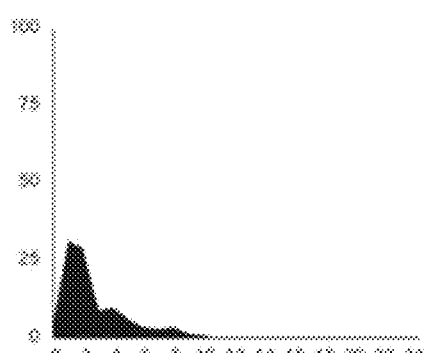
Figure 8G:
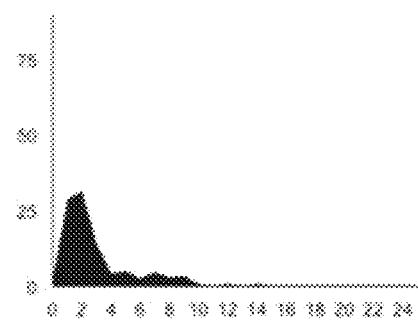
Figure 8H:
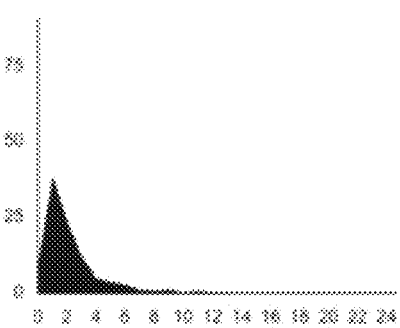

FIGS. 6e and 6f show the results obtained using the method of the present invention (FIG. 6e shows the results obtained when the method is carried out in a facility wherein the injection unit is a nebuliser and FIG. 6f shows the results obtained when the method is carried out in a facility wherein the injection unit is an electronebuliser). As shown in said figures, a significant reduction in the size of the microcapsules and an improvement in their monodispersity is observed upon using the method and facility of the present invention.

Likewise, table 5 shows a sampling study carried out by mixing a fixed amount of omega-3 microcapsules with powdered milk and water. A mixture of powdered milk and water was used as a sampling reference and the nomenclature followed to rate the samples was the following:
  0: No differences with respect to the reference.
  1: Small differences with respect to the reference.
  3: Clear differences with respect to the reference.
  5: Major differences with respect to the reference.

TABLE 5

Omega-3 microcapsule sampling results.

| SAMPLE | SAMPLE COLOUR (T = 0 DAYS) | SAMPLE COLOUR (T = 100 DAYS) | FISH OIL SMELL (T = 0 DAYS) | FISH OIL SMELL (T = 100 DAYS) | FISH OIL FLAVOUR (T = 0 DAYS) | FISH OIL FLAVOUR (T = 100 DAYS) | SAMPLE DISPERSION (T = 0 DAYS) | SAMPLE DISPERSION (T = 100 DAYS) |
|---|---|---|---|---|---|---|---|---|
| BASF | 0 | 0 | 0 | 1 | 0 | 1 | 0 | 0 |
| LIFE | 0 | 0 | 0 | 1 | 0 | 1 | 0 | 0 |
| MEG | 0 | 0 | 0 | 1 | 1 | 3 | 0 | 0 |
| STEPAN | 0 | 0 | 0 | 1 | 0 | 1 | 0 | 0 |
| Example 1.1 | 0 | 0 | 0 | 0 | 0 | 0 | 0 | 0 |
| Example 1.2 | 0 | 0 | 0 | 0 | 0 | 0 | 0 | 0 |

Examples 2.1 and 2.2 describe non-limiting methods for encapsulating *Lactobacillus rhamnosus* probiotics and describe the corresponding viability studies.

Example 2.1 Encapsulation of a Probiotic Using a Nebuliser as an Injector

In this exemplary embodiment, a nebuliser was used as an injection unit and milk serum protein as a polymer to encapsulate the probiotic. FIG. 7a shows a SEM micrograph showing the microcapsules obtained and FIG. 7b shows a graph with the size distribution obtained. Table 6 shows the experimental parameters and ranges of use of this example.

TABLE 6

Experimental parameters and operating ranges of the processing of example 2.1 using a solution comprising milk serum protein, Tego ® and whole milk.

| | Minimum value | Maximum value |
|---|---|---|
| Parameters | | |
| Solution flow rate | 1 mL/h | 50 L/h |
| Air flow rate | 1 LPM | 500 LPM |
| Drying gas flow rate | 10 m³/h | 100,000 m³/h |
| Solution | | |
| LR | 0.05% w/w | 50% w/w |
| WHS | 0.05% w/w | 50% w/w |
| Tego | 0.01% w/w | 10% w/w |
| Whole milk | solvent | Solvent |

Example 2.2 Encapsulation of a Probiotic Using an Electronebuliser as an Injector In this case, an electronebuliser as an injection unit was used and the same natural polymer (milk serum protein) as in example 2.1 was used. FIGS. 8a-8d show SEM micrographs of the microcapsules obtained by applying different electric current values (more specifically, without applying electric current, applying 1 kV, 5 kV and 10 kV, respectively). Additionally, FIGS. 8e-8h show the value of the size of the microcapsules obtained in said cases. Table 7 shows the experimental parameters and ranges of use of this example.

FIG. 8 shows the effect of adding the bacterium on microcapsule size.

TABLE 7

Experimental parameters and operating ranges of the processing of example 2.2 using a solution comprising milk serum protein, Tego ® and whole milk, without using electric current and using a 10 kV electric current.

| | Minimum value | Maximum value |
|---|---|---|
| Parameters | | |
| Solution flow rate | 1 mL/h | 50 L/h |
| Air flow rate | 1 LPM | 500 LPM |

TABLE 7-continued

Experimental parameters and operating ranges of the processing of example 2.2 using a solution comprising milk serum protein, Tego ® and whole milk, without using electric current and using a 10 kV electric current.

| | Minimum value | Maximum value |
|---|---|---|
| Drying gas flow rate | 10 $m^3/h$ | 100,000 $m^3/h$ |
| Voltage | 0 kV | 500 kV |
| Solution | | |
| LR | 0.05% w/w | 50% w/w |
| WHS | 0.05% w/w | 50% w/w |
| Tego | 0.01% w/w | 10% w/w |
| Whole milk | solvent | solvent |

Figure 9:
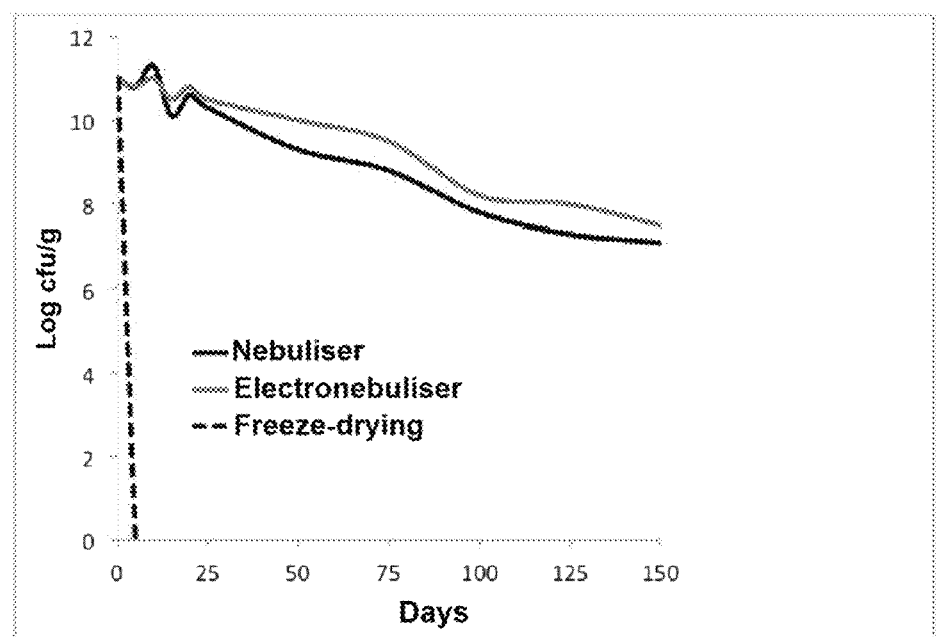
FIG. 9. Shows a viability study presenting a comparison between *Lactobacillus rhamnosus* microparticles obtained by freeze-drying according to a standard method using maltodextrin as a cryoprotector and microparticles obtained using the described method and facility when the injection unit is a nebuliser and when it is an electronebuliser.

Likewise, FIG. 9 presents a viability study showing how encapsulation by means of the facility of the present invention, in examples 2.1 and 2.2 using an electronebuliser, has better viability than encapsulation using a nebuliser.

Additionally, as can be observed in the figure, both encapsulation using an electronebuliser and encapsulation using a nebuliser show better results than those obtained using the technique known as freeze-drying, which is that represented as the reference technique.

The results shown are for the encapsulation of a *Lactobacillus rhamnosus* probiotic, taking a freeze-dried model sample of this type of probiotic (1%) and maltodextrin (10%) in a phosphate-buffered saline solution as a reference.

The invention claimed is:

1. A method for the industrial encapsulation of thermolabile substances characterised in that it is carried out in a facility for industrial drying and/or encapsulation of thermolabile substances comprising at least:

one injection unit comprising at least:
- one inlet for a solution;
- one inlet for injection gas; and
- one outlet for droplets through which sprayed droplets of solution are released, one drying unit arranged after the injection unit and comprising at least:
- one inlet for drying gas;
- one inlet for droplets;
- one longitudinal receptacle through which the droplets with the drying gas move until the solvent of the droplets evaporates, forming microcapsules; and
- one outlet for microcapsules and drying gas through which the microcapsules and drying gas that drags the evaporated solvent with it are released from the receptacle;

one collection unit arranged after the drying unit, which is configured to separate the microcapsules generated from the drying gas;

wherein the method comprises the following stages:

a) preparing a polymer solution comprising:
- a thermolabile substance to be encapsulated,
- an encapsulating precursor;
- an organic or aqueous solvent selected from ethanol, water and a combination thereof; and b) forming droplets from a polymer solution obtained in stage (a) in the presence of an injection gas flow;

c) drying the droplets obtained in stage (b) in the drying unit at a controlled temperature to obtain microcapsules; and d) collecting the microcapsules obtained in stage (c) by means of the collection unit; and wherein the stage b) of forming droplets is carried out by applying a voltage of between 0.1 kV and 500 kV to the solution and injection gas flow at the outlet of the injection unit.

2. The method of claim 1, wherein the stage c) is carried out at ambient or sub-ambient temperature.

3. The method of claim 1, wherein the encapsulating precursor of stage (a) is selected from animal, vegetable and microbial proteins.

4. The method of claim 3, wherein the encapsulating precursor of stage (a) is selected from milk serum, caseins, natural polypeptides or obtained from the genetic modification of microorganisms, collagen, soy protein and zein.

5. The method of claim 1, wherein the encapsulating precursor of stage (a) are oligosaccharides selected from lactose, sucrose, maltose and fructo-oligosaccharides.

6. The method of claim 1 wherein an additive is used in stage a).

7. The method of claim 6, wherein the additive is a surfactant.

8. The method of claim 1, wherein the stage b) of forming droplets is carried out by applying a voltage of between 5 kV and 15 kV to the solution and injection gas flow at the outlet of the injection unit.

9. The method of claim 1, wherein the stage b) of forming droplets is carried out by applying a voltage in alternating current.

* * * * *